(12) United States Patent
Alocilja et al.

(10) Patent No.: US 10,359,378 B2
(45) Date of Patent: Jul. 23, 2019

(54) NUCLEAR MAGNETIC RESONANCE APPARATUS, SYSTEMS, AND METHODS

(71) Applicant: BOARD OF TRUSTEES OF MICHIGAN STATE UNIVERSITY, East Lansing, MI (US)

(72) Inventors: Evangelyn C. Alocilja, East Lansing, MI (US); Yilun Luo, Ann Arbor, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 1288 days.

(21) Appl. No.: 14/400,996

(22) PCT Filed: May 13, 2013

(86) PCT No.: PCT/US2013/040713
§ 371 (c)(1),
(2) Date: Nov. 13, 2014

(87) PCT Pub. No.: WO2013/173207
PCT Pub. Date: Nov. 21, 2013

(65) Prior Publication Data
US 2015/0168322 A1 Jun. 18, 2015

Related U.S. Application Data

(60) Provisional application No. 61/646,426, filed on May 14, 2012.

(51) Int. Cl.
*G01V 3/00* (2006.01)
*G01N 24/08* (2006.01)
(Continued)

(52) U.S. Cl.
CPC ............. *G01N 24/08* (2013.01); *G01R 33/28* (2013.01); *G01R 33/302* (2013.01); *G01R 33/448* (2013.01)

(58) Field of Classification Search
CPC ...................................................... G01R 33/32
(Continued)

(56) References Cited

U.S. PATENT DOCUMENTS

| 4,425,547 A | 1/1984 | Sugimoto |
| 4,695,798 A | 9/1987 | Brandes |

(Continued)

OTHER PUBLICATIONS

International Search Report in PCT/US2013/040713, dated Nov. 8, 2013 (3 pages).

*Primary Examiner* — Louis M Arana
(74) *Attorney, Agent, or Firm* — Marshall, Gerstein & Borun LLP

(57) ABSTRACT

In one aspect, the disclosure relates to a nuclear magnetic resonance transceiver including: (a) a variable-frequency electromagnetic signal generator with (i) a frequency input and (ii) an EM signal output; (b) an electronic frequency controller including (i) a frequency output coupled to the frequency input of the variable-frequency EM signal generator, (ii) an intermediate frequency set-point input, and (iii) an intermediate frequency measurement input; (c) an NMR transmission probe with an EM signal input coupled to the EM signal output of the variable-frequency EM signal generator; (d) an NMR receiving probe with an EM signal output; and (e) an electronic mixer with (i) a first input coupled to the EM signal output of the NMR receiving probe, (ii) a second input coupled to the EM signal output of the variable-frequency EM signal generator, and (iii) a mixed EM signal output coupled to the frequency measurement input of the frequency controller.

27 Claims, 3 Drawing Sheets

(51) Int. Cl.
*G01R 33/30* (2006.01)
*G01R 33/28* (2006.01)
*G01R 33/44* (2006.01)

(58) Field of Classification Search
USPC .................................. 324/322, 318
See application file for complete search history.

(56) References Cited

U.S. PATENT DOCUMENTS

| | | | |
|---|---|---|---|
| 5,166,620 A | 11/1992 | Panosh | |
| 5,442,292 A * | 8/1995 | Kolem | G01R 33/3607 |
| | | | 324/318 |
| 6,242,915 B1 | 6/2001 | Hurd | |
| 6,252,405 B1 | 6/2001 | Watkins et al. | |
| 6,259,253 B1 * | 7/2001 | Ellingson | G01R 33/3621 |
| | | | 324/322 |
| 6,304,085 B2 * | 10/2001 | Kuth | G01R 33/3607 |
| | | | 324/318 |
| 6,577,125 B2 | 6/2003 | Prammer et al. | |
| 6,803,761 B2 | 10/2004 | Prammer et al. | |
| 7,474,976 B2 | 1/2009 | Schenkel et al. | |
| 8,988,076 B2 * | 3/2015 | Mandal | G01R 33/3621 |
| | | | 324/318 |
| 2002/0075000 A1 | 6/2002 | Prammer et al. | |
| 2003/0153094 A1 | 8/2003 | Alocilja et al. | |
| 2004/0014236 A1 | 1/2004 | Albo et al. | |
| 2007/0210798 A1 | 9/2007 | Race et al. | |
| 2008/0284470 A1 | 11/2008 | Park et al. | |
| 2008/0314766 A1 | 12/2008 | Alocilja et al. | |
| 2009/0123939 A1 | 5/2009 | Alocilja et al. | |
| 2009/0224762 A1 | 9/2009 | Mehr et al. | |
| 2010/0160173 A1 | 6/2010 | Mchale et al. | |
| 2010/0256481 A1 | 10/2010 | Mareci et al. | |
| 2011/0020787 A1 | 1/2011 | Lee | |
| 2011/0057654 A1 | 3/2011 | Sun et al. | |
| 2011/0091987 A1 | 4/2011 | Weissleder et al. | |

\* cited by examiner

NUCLEAR MAGNETIC RESONANCE APPARATUS, SYSTEMS, AND METHODS

CROSS REFERENCE TO RELATED APPLICATION

Priority is claimed to U.S. Provisional Application No. 61/646,426 (filed on May 14, 2012), which is incorporated herein by reference in its entirety.

STATEMENT OF GOVERNMENT INTEREST

This invention was made with government support under 2007-ST-061-000003 awarded by the Department of Homeland Security. The government has certain rights in the invention.

BACKGROUND OF THE DISCLOSURE

The disclosure relates to nuclear magnetic resonance (NMR) transceivers and related apparatus, in particular for portable, field-operable biosensor devices. The disclosed devices can be used for rapid on-field detection of disease-causing agents, including bacteria, viruses, DNA, proteins, toxins, chemicals and other contaminants for healthcare, defense, and safety applications.

Sun et al. U.S. Publication No. 2011/0057654 and Weissleder et al. U.S. Publication No. 2011/0091987 relate to NMR transceivers, systems, and methods.

Alocilja et al. U.S. Publication Nos. 2003/0153094, 2008/0314766, 2009/0123939, relate to biosensor devices and/or biologically enhanced, electrically active magnetic (BEAM) nanoparticle compositions and are incorporated herein by reference in their entireties.

SUMMARY

The disclosure relates to nuclear magnetic resonance (NMR) transceivers and related apparatus. In an embodiment, a handheld NMR-based biosensor utilizes magnetic nanoparticles as a biomarker for label-free detection of target bio-materials in complex sample matrices. The NMR biosensor operates at 0.47 Tesla of magnetic strength with an embedded power and frequency control to compensate for temperature fluctuations, which can cause significant frequency drift of the NMR signal. It is small, ultra-sensitive, accurate, and field-operable for rapid detection and diagnosis of infectious agents and other contaminants.

In one aspect, the disclosure relates to a nuclear magnetic resonance (NMR) transceiver 100 comprising: (a) a variable-frequency electromagnetic (EM) signal generator 10 (e.g., a pulse or sinusoidal signal generator, such as a direct digital synthesizer) comprising (i) a frequency input and (ii) an EM signal output; (b) an electronic frequency controller 60 comprising (i) a frequency output 62 coupled to the frequency input of the variable-frequency EM signal generator 10, (ii) an intermediate frequency set-point input 64, and (iii) an intermediate frequency measurement input 66; (c) an NMR transmission probe 42 comprising an EM signal input coupled to the EM signal output of the variable-frequency EM signal generator 10; (d) an NMR receiving probe 44 comprising an EM signal output; and (e) an electronic mixer 50 (e.g., multiplying mixer) comprising (i) a first input coupled to the EM signal output of the NMR receiving probe 44, (ii) a second input coupled to the EM signal output of the variable-frequency EM signal generator 10, and (iii) a mixed EM signal output coupled to the frequency measurement input of the frequency controller 60.

In general, coupling of components can indicate electronic/electric coupling between two or more electronic/electric components, with or without intervening components such as filters (e.g., low-, high-, band-pass), power amplifiers, electronic controllers (e.g., P, PI, PD, PID), converters (e.g., ADC, DAC), impedance matching circuitry, signal measurement components (e.g., oscilloscope), directional couplers, switches in an ON state (cf. switches in an OFF state for selectable de-coupling between components). Coupling between two components can be direct or indirect (e.g., with one or more intervening components) and/or physical (e.g., wired, electrically connected components within an integrated circuit) or remote (e.g., wirelessly connected components).

Various refinements and extensions of the NMR transceiver 100 are possible. For example, the variable-frequency EM signal generator can be capable of delivering an EM signal to the NMR transmission probe 42 input with a power ranging from 1 W to 100 W (e.g., at least 1, 2, 5, 10 W and/or up to 10, 20, 50, 100 W; such as alone or in combination with a coupled amplifier). Similarly, the variable-frequency EM signal generator 10 can be capable of generating an EM signal with a frequency ranging from 5 Hz to 200 MHz (e.g., at least 5, 10, 20 MHz and/or up to 50, 100, 200 MHz; such as with tuning accuracy up to and/or at least 0.1, 1, or 10 µHz).

In one refinement, (i) the NMR transmission probe 42 and the NMR receiving probe 44 are in the form a combined NMR probe 40 (e.g., a solenoid coil) coupled to a switch switchable between at least a transmit state and a receive state; (ii) in the transmit state (e.g., transmit ON, receive OFF), the NMR probe 40 is coupled to the EM signal output of the variable-frequency EM signal generator 10; and (iii) in the receive state (e.g., transmit OFF, receive ON), the NMR probe 40 is coupled to the first input of the mixer 50.

In another refinement, the NMR transceiver 100 further comprises: (f) a linear power amplifier 20 comprising (i) an EM signal input coupled to the signal output of the variable-frequency EM signal generator 10 and (ii) an amplified EM signal output coupled to the EM signal input of the NMR transmission probe 42 (e.g., coupled to a variable-gain controller as described below). More specifically, the NMR transceiver 100 can further comprise: (f) a linear power amplifier 20 comprising (i) an EM signal input coupled to the signal output of the variable-frequency EM signal generator 10, (ii) an amplifier gain input, and (iii) an amplified EM signal output; (g) a directional coupler 22 comprising (i) an EM signal input coupled to the amplified EM signal output of the power amplifier 20, (ii) an EM signal output coupled to the EM signal input of the NMR transmission probe 42, and (iii) a voltage output (e.g., representing the voltage reflected back from the NMR (transmission) probe 40, where the set-point can be zero to reflect no reflected voltage from the NMR probe 40); and (h) an electronic gain controller 30 comprising (i) a gain output 32 coupled to the amplifier gain input of the power amplifier 20, (ii) a voltage set-point input 34, and (iii) a voltage measurement input 36 coupled to the voltage output of the directional coupler 22.

In another aspect, the disclosure relates to a nuclear magnetic resonance (NMR) apparatus comprising: (a) the NMR transceiver 100 according to any of the various disclosed embodiments; (b) a magnet 70 having a magnetic field; and (c) a sample container 80 positionable in the magnetic field and proximate to the NMR transmission probe 42 and the NMR receiving probe 44. In a refinement, (i) the NMR transceiver 100 comprises the combined NMR probe 40; and (ii) the sample container 80 is mountable to the NMR probe 40 (e.g., a NMR sample tube or other container that is removably mounted within a solenoid coil of the NMR probe 40) In another refinement, the magnet comprises a permanent magnet (e.g., a permanent magnet with the given magnetic field; in other embodiments, the magnet can be an electromagnet capable of generating the given field). In another refinement, the magnetic field ranges in strength from 0.01 T to 1 T (e.g., at least 0.01, 0.02, 0.05, 0.1, 0.2, 0.4 T and/or up to 0.1, 0.2, 0.4, 0.6, 0.8, 1 T).

In another aspect, the disclosure relates to a method for measuring nuclear magnetic resonance (NMR) in a sample, the method comprising: (a) providing the NMR apparatus/transceiver 100 according to any of the various disclosed embodiments; (b) selecting the frequency set-point input 64 to the frequency controller 60; (c) placing a sample to be measured for the presence of a magnetic moiety in the sample container 80; (d) exciting the sample with an EM pulse signal delivered from the NMR transmission probe 42, the EM (pulse) signal having a selected frequency 62 and a selected power (e.g., defined by power gain 32); (e) detecting an NMR signal emitted from the excited sample with the NMR receiving probe 44; (f) determining a new selected frequency 62 for the EM pulse signal delivered from the NMR transmission probe 44 with the frequency controller 60 and an error function determined from (i) the frequency set-point input 64 and (ii) a mixed EM signal from the delivered EM (pulse) signal and the emitted NMR signal as the frequency measurement input 66; and optionally (g) determining whether the magnetic moiety is present in the sample (e.g., the moiety itself and/or a target analyte bound to the moiety; such as by measuring a relaxation property of the emitted NMR signal such as $T_1$ or $T_2$ (or $T_2^*$) relaxation times). Steps (d)-(f) can be repeated/iterated any desired number of times to minimize/reduce the error function, such as before determining whether the magnetic moiety or other target analyte is present in the sample. Similarly, when the NMR transceiver 100 comprises the power amplifier 20, the directional coupler 22, and the gain controller 30, the method can further comprise determining a new selected power (e.g., power gain 32) for the EM pulse signal delivered from the NMR transmission probe 42 with the gain controller 30 and an error function determined from (A) the voltage set-point input 34 and (B) the voltage output from the directional coupler as the voltage measurement input 36.

Various refinements and extensions of the magnetic moiety are possible. For example, the magnetic moiety can comprise a magnetic nanoparticle bound to a target analyte (e.g., with a specific or non-specific binding pair member for the target analyte that is itself immobilized or otherwise bound to the magnetic nanoparticle), for example in the form of a magnetic nanoparticle-analyte complex or conjugate including the magnetic nanoparticle bound to the target analyte. In an embodiment, the sample is substantially free from magnetic nanoparticles not bound to the target analyte (e.g., unbound magnetic nanoparticles have been separated from the sample prior to analysis but subsequent to formation of the magnetic nanoparticle-analyte complex such that magnetic nanoparticles present in the sample essentially only correspond to those that are complexed with the target analyte). In another embodiment, the sample further comprises magnetic nanoparticles not bound to the target analyte (e.g., eliminating a separation step between excess unbound magnetic nanoparticles and analyte-complexed magnetic nanoparticles after complex formation). For example, excess unbound magnetic nanoparticles present in the sample medium after complexation of some magnetic nanoparticles with target analyte are allowed to remain such that at least some unbound magnetic nanoparticles are present in the sample when the NMR apparatus is used to detect the magnetic nanoparticle (e.g., differentiating between unbound magnetic nanoparticles and analyte-complexed magnetic nanoparticles, such as with reference to a control sample of unbound magnetic nanoparticles with a concentration equal to that of the unbound magnetic nanoparticles initially added to the analyte-containing sample). In a refinement of this embodiment, the method can further comprise repeating the method for measuring for nuclear magnetic resonance in a separately analyzed control sample, the control sample comprising magnetic nanoparticles (i) only in the form of magnetic nanoparticles not bound to the target analyte (e.g., being free from analyte and/or magnetic nanoparticle-analyte complexes) and (ii) in the same amount as total magnetic nanoparticles present in the sample (e.g., magnetic nanoparticles initially added to the sample to be tested, at least some of which conjugate with any analyte present therein prior to NMR analysis); and comparing the NMR measurement for the sample with the NMR measurement for the control sample to determine whether the magnetic nanoparticle-analyte complex is present in the sample (e.g., and whether analyte was present in the original sample prior to conjugation, such as based on a difference in NMR measurements between the sample and the control sample). In various embodiments, the target analyte is selected from the group consisting of bacteria, viruses, oligonucleotides, polynucleotides, proteins, enzymes, and combinations thereof (e.g., generally a single selected member or members within a group and capable of binding to the binding pair member of the magnetic nanoparticles). In another embodiment, the magnetic nanoparticle comprises: (i) a magnetic nanoparticle core, (ii) a conductive polymer shell bound to the magnetic nanoparticle core, and (iii) a binding pair member bound to the conductive polymer shell (e.g., a binding pair member bound to the target analyte in the form of an analyte conjugate with the magnetic nanoparticle). In various other embodiments, (i) the magnetic nanoparticles comprise ferromagnetic nanoparticles such as Fe(II) and/or Fe(III); (ii) the conductive polymer is selected from the group consisting of polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, conductive carbohydrates, conductive polysaccharides, derivatives thereof, combinations thereof, blends thereof with other polymers, and copolymers of the monomers thereof; and/or (iii) the binding pair member is selected from the group consisting of antibodies, antibody fragments, antigens, biotin, avidin and derivatives thereof, hormones, hormone receptors, polynucleotides, oligonucleotides, aptamers, whole cells, and combinations thereof.

Other refinements and extensions of the methods are possible. For example, the frequency set-point input 64 can be selected to correspond to the ambient temperature during measurement (e.g., the sample temperature and/or environmental temperature, such as from a pre-calibrated table of frequency set-points as a function of temperature). In an embodiment, frequency set-point input 64 can be selected to have a value ranging from 0.01 kHz to 10 kHz (e.g., at least 0.01 kHz, 0.1 kHz, 0.2 kHz, or 0.5 kHz and/or up to 1 kHz, 2 kHz, 5 kHz, or 10 kHz). In an embodiment, the sample comprises a liquid sample medium (e.g., an aqueous medium including at least some water or containing mostly water; can include the raw sample matrix to be tested for presence of the magnetic moiety or analyte, such as milk, culture broth, biological fluid from an organism (e.g., blood, saliva)). In a refinement, the method can be performed without active and/or passive temperature control (e.g., NMR transceiver and/or apparatus need not include passive temperature control such as insulation or active temperature control such as via heat exchange apparatus to maintain the sample and/or apparatus environment at a constant or specified temperature).

In another aspect, the disclosure relates to a nuclear magnetic resonance (NMR) measurement system comprising: (a) the NMR apparatus and/or transceiver according to any of the various disclosed embodiments; and (b) a computer comprising a processor and memory coupled to a computer readable storage medium encoded with a computer program, the program comprising instructions that, when executed by the processor, cause the computer to control the NMR apparatus and execute any, some, or all of the variously disclosed method steps for measuring an NMR signal in a sample.

In another aspect, the disclosure relates to a method for determining the presence of a target analyte in a sample, the method comprising: (a) analyzing a first (e.g., unknown) sample comprising (or suspected of comprising) metal nanoparticles for the presence of a magnetic moiety by measuring nuclear magnetic resonance (NMR) (e.g., using the methods and/or apparatus disclosed herein to measure an NMR emission signal from the sample), the first sample having a first (e.g., known) amount (e.g., concentration) of magnetic nanoparticles, wherein the magnetic nanoparticles are in the form of magnetic nanoparticles not bound to the target analyte, magnetic nanoparticles complexed with the target analyte, or a combination thereof; (b) analyzing a second (e.g., known/control) sample comprising metal nanoparticles for the presence of a magnetic moiety by measuring NMR, the second sample having a second (e.g., known) amount (e.g., concentration) of magnetic nanoparticles equal to the first amount of magnetic nanoparticles in the first sample, wherein the magnetic nanoparticles are only in the form of magnetic nanoparticles not bound to the target analyte; and (c) comparing analysis results from the first sample and the second sample to determine whether analyte-magnetic nanoparticle complexes are present in the first sample (e.g., where a change in NMR emission signal between the samples indicates the presence of the analyte complex, such as with a reduction in the ($T_2$) relaxation time relative to the control; optionally quantifying same with a calibration curve).

Additional features of the disclosure may become apparent to those skilled in the art from a review of the following detailed description, taken in conjunction with the drawings, examples, and appended claims.

DESCRIPTION OF THE DRAWINGS

The following detailed description of the various disclosed methods, processes, systems, and apparatus refers to the accompanying drawings in which.

Figure 1:
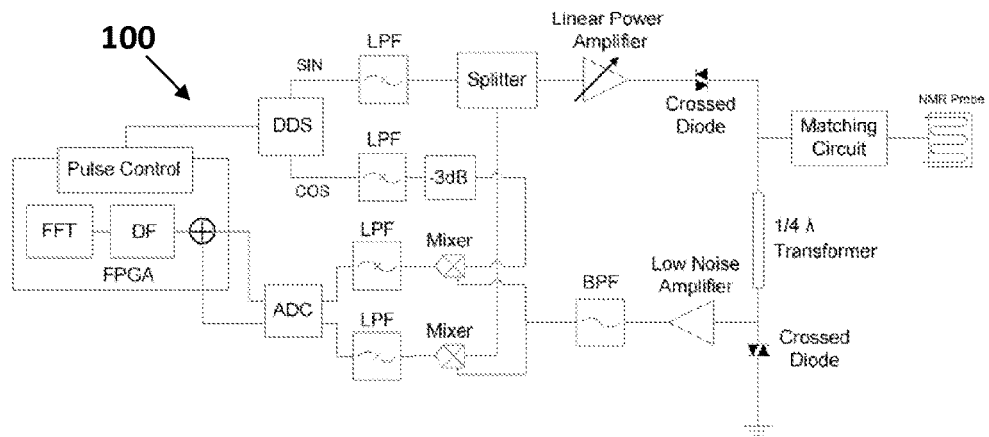
FIG. 1 is a schematic illustrating the hardware system structure for a portable NMR transceiver according to the disclosure.

While the disclosed processes, compositions, systems, apparatus, and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The representative NMR apparatus described below has a field-programmable gate array (FPGA) for embedded concurrent signal processing and precision NMR pulse control, robust temperature control in the form of excitation pulse frequency and amplification gain feedback control for field operation, and a direct digital synthesizer (DDS) for generating varying frequencies and complex waveforms. In the disclosed embodiment, a magnet is selected for homogeneity and/or field strength characteristics to optimize the signal-to-noise ratio (SNR) of the NMR apparatus. The selected power amplifier is capable of 20 Watts output power. In the illustrated biosensing application, electrically active magnetic nanoparticles are used for extracting and labeling a target analyte such as a target bacterium of interest.

NMR Transceiver and Apparatus

The portable NMR based on the FPGA is designed with variable output power (0 to 50 Watts) and frequency range from 5 MHz to 50 MHz. It has embedded power and frequency control to stabilize the device from temperature fluctuation. An embedded system in the FPGA provides for signal processing and digital quadrature amplitude demodulation (QAM) to improve sensitivity by detecting NMR frequency and phase information. The NMR excitation signal is generated using the DDS with maximum frequency of 200 MHz and frequency tuning accuracy of 1 µHz. With excellent concurrent calculation capability, the embedded system in the FPGA can implement a multi layer state machine to control DDS frequency and amplifier gain, and to provide precise NMR pulse control. System structure of the hardware for a representative NMR transceiver 100 according to the disclosure is shown in FIG. 1.

The magnetic field strength of an NMR magnet is very sensitive to changes in ambient temperature. For example, a 0.5 Tesla PM-1055 magnet (available from MetroLab, Inc.) has a temperature coefficient of 1200 ppm/K. Hence, a temperature change of 10° C. induces 238.9 kHz shift in the NMR Larmor frequency. An NMR system is generally designed as a high-Q transceiver in order to detect the nucleus signal in micro volts. This large frequency shift in the appropriate NMR excitation frequency, however, can significantly reduce NMR excitation energy delivered to the sample and can degrade signal demodulation performance, which can result in a large signal attenuation (e.g., potentially resulting in wrong detections such as false positives, false negatives, or miscalculated sample concentrations for a target analyte). Thus, NMR biosensor sensitivity can be significantly affected, and its on-field application can be limited without sufficient means to compensate for temperature fluctuations.

Figure 2:
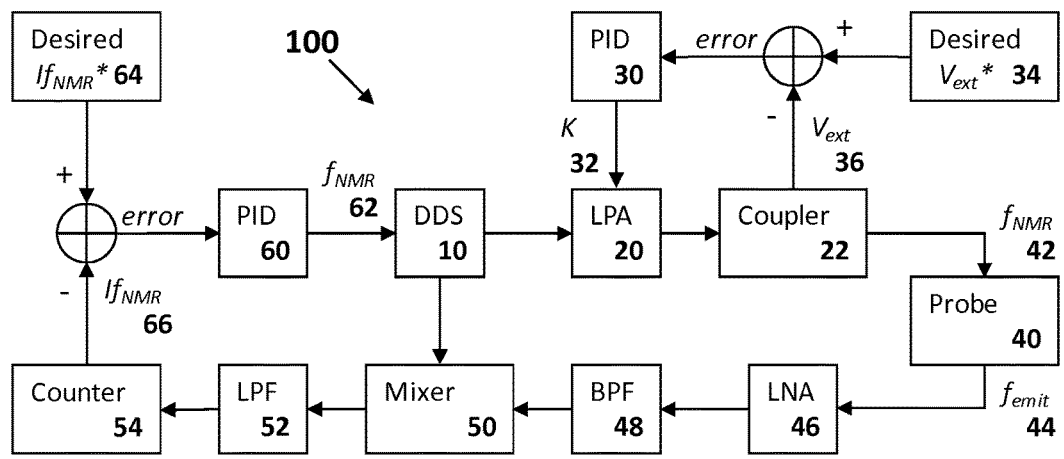
FIG. 2 is a block diagram illustrating the NMR frequency control and power control for an NMR transceiver according to the disclosure.

To automatically compensate for the ambient environmental (temperature) effect, an embedded control is designed including NMR frequency control and NMR power control, which is shown in FIG. 2 as an NMR transceiver 100. The NMR frequency controller 60 (illustrated as a PID controller) detects the frequency shift ($f_{emit}$) from the NMR receiver 44, and optimally compensates this error by adjusting the output frequency ($f_{NMR}$) in the NMR transmitter 42. The NMR power controller 30 (also illustrated as a PID controller) balances the amplitude of the received NMR signal ($f_{NMR}$) by controlling the output power of the DDS variable-frequency electromagnetic signal generator 10.

The transmitter frequency 42 ($f_{NMR}$) is set by the DDS module/generator 10. However, the frequency of the re-emitted NMR signal 44 ($f_{emit}$) is determined by the magnetic field strength of the NMR magnet (e.g., where a characteristic resonant Larmor frequency of the emission is a function of nuclei-specific parameters and is proportional to the magnetic field strength, B). The magnet's magnetic field strength is a sensitive function of temperature and can fluctuate substantially with small changes in the ambient temperature (e.g., uncontrolled external environment in which sample is analyzed and where an (average) temperature can be at least 5° C., 10° C., 15° C., or 20° C. and/or up to 25° C., 30° C., 35° C., or 40° C., and where the temperature can fluctuate within 1° C., 2° C., 5° C., or 10° C. over a measurement period of at least 5 min, 10 min, or 30 min and/or up to 2 hour, 4 hour, or 8 hour).

For improved NMR accuracy and sensitivity, the frequency 62 ($f_{NMR}$) set by the DDS module 10 can be set with a positive offset relative to that of the emitted NMR signal frequency 44 ($f_{emit}$). Suitably, the offset $\Delta f$ ($f_{NMR}-f_{emit}$) is desirably positive and on the order of a kHz frequency, for example at least 0.01 kHz, 0.1 kHz, 0.2 kHz, or 0.5 kHz and/or up to 1 kHz, 2 kHz, 5 kHz, or 10 kHz. Thus, the measured input frequency 66 ($IF_{NMR}$) to the controller 60, for example after a (multiplying) mixer 50 and a low-pass filter (LPF) module 52 as measured by a counter 54, is also desirably on the order of a kHz frequency similar to that of $\Delta f$ (although it can be outside the desired range due to temperature fluctuations). The NMR signal can be amplified by a low-noise amplifier (LNA) 44 and a filtered with a high Q (quality; low bandwidth) bandpass filter (BPF) 48 prior to passing to the mixer 50. The cut-off frequency of the LPF 52 can be selected based on the desired frequency offset so that it reflects the differential frequency output (e.g., and not the additive frequency output, such as ($f_{NMR}-f_{emit}$) but not ($f_{NMR}+f_{emit}$) for the output signal) of the mixer 50. For example the cut-off frequency can be at least 0.01 kHz, 0.1 kHz, 0.2 kHz, or 0.5 kHz and/or up to 1 kHz, 2 kHz, 5 kHz, or 10 kHz (e.g., generally larger than that of the desired offset $\Delta f$ (or $IF_{NMR}*$)).

During operation of the NMR apparatus in the field, the temperature could change substantially within hours. For example, a temperature change of 1° C. induces a 23.89 kHz shift in the NMR Larmor frequency (i.e., 19.91 MHz×(1200/$10^6$)=23.89 kHz). Such a substantial frequency change typically would exceed the cut-off frequency of the LPF 52, causing significant signal attenuation and measurement error in NMR signal decay rate.

The NMR transceiver 100 compensates for such temperature fluctuations with a set-point input frequency 64 ($IF_{NMR}*$) to the controller 60. The controller 60 automatically compensates for the measured frequency difference 66 ($IF_{NMR}$) and maintains it at a desired value. For example, the set-point $IF_{NMR}*$ is desirably set on the order of a kHz frequency, for example at least 0.01 kHz, 0.1 kHz, 0.2 kHz, or 0.5 kHz and/or up to 1 kHz, 2 kHz, 5 kHz, or 10 kHz (e.g., suitably a constant set-point value within a desired range over a measurement period of at least 5 min, 10 min, or 30 min and/or up to 2 hour, 4 hour, or 8 hour). The counter 54 after the LPF 52 can measure the frequency of the $IF_{NMR}$ signal in real-time. Then, the controller 60 generates an error function ($IF_{NMR}*-IF_{NMR}$), and the controller 60 uses the error function to optimally increase or decrease the NMR transmitter's frequency 62/42 ($f_{NMR}$) to maintain/adjust $IF_{NMR}$ to its desired value (e.g., using standard control logic such as with a P, PI, PD, or PID electronic controller).

A linear power amplifier (LPA) 20 is controlled with a gain controller 30, as the NMR probe 40 exhibits optimal performance for a specific frequency at a narrow band. As described above, after a temperature change/fluctuation, the transmitter's frequency 62/42 ($f_{NMR}$) is adjusted by the controller 60. As a result, the energy delivered to the sample inside the NMR probe 40 would be attenuated by the NMR probe 40. This would result in attenuation in re-emitted NMR signal 44 ($f_{emit}$) and finally cause a measurement error in the NMR signal's decay rate. A directional coupler 22 can be used to measure the actual energy 36 ($V_{ext}$) delivered to a sample by the NMR probe 40. The controller 30 can automatically decrease or increase the gain 32 (K) to the amplifier 20 to maintain a consistent level of energy delivered to the probe 40. The voltage set-point input 34 (Desired $V_{ext}*$) is a suitable voltage selected for application to the sample in the NMR probe 40, such as about 70 V peak-to-peak (e.g., more generally at least 1 V, 10 V, 20 V, or 50 V and/or up to 20 V, 50 V, or 100 V peak-to-peak), and a corresponding error function ($V_{ext}*-V_{ext}$) is used by the controller 30 (e.g., a P, PI, PD, or PID controller) to adjust the gain and maintain the output voltage ($V_{ext}$) at or near the desired voltage ($V_{ext}*$).

Figure 3:
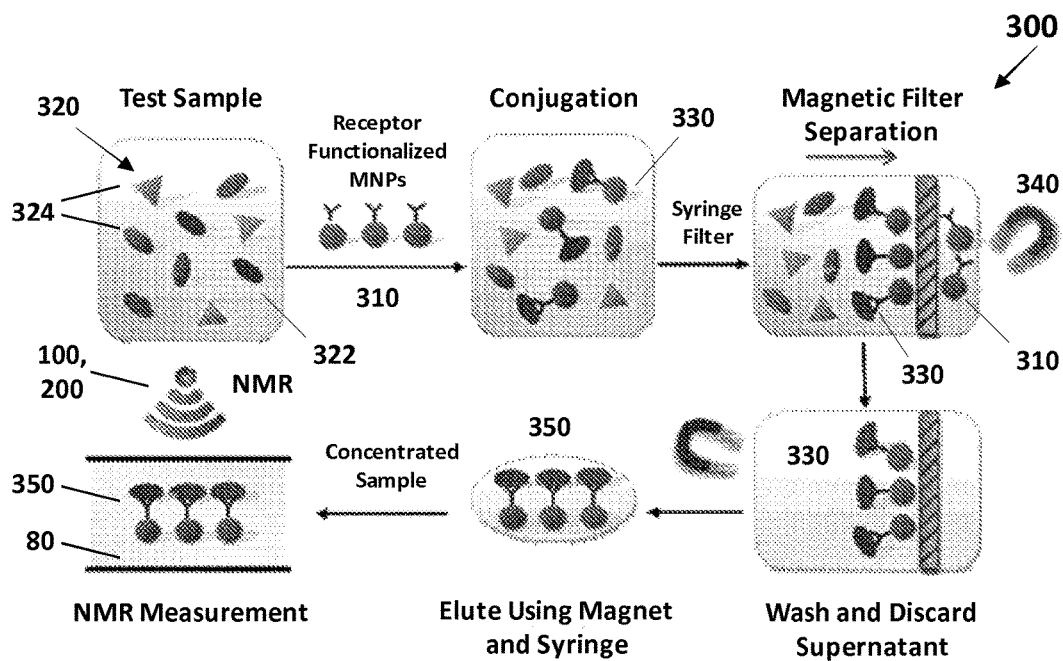
FIG. 3 illustrates a method for capturing/conjugating, separating, and detecting a target analyte in a sample using an NMR apparatus according to the disclosure.

The NMR transceiver 100 can be used in an NMR biosensing apparatus 200 utilizing antibody-functionalized magnetic nanoparticles 310 to extract target materials from complex sample matrices 320 potentially including target analytes 322 and/or non-target components 324, for example as illustrated in FIG. 3 in a method 300 for extracting target analytes 322 from an initial sample volume 320 to prepare a sample extract 350 for NMR analysis. The synthesized bio-functionalized magnetic nanoparticles (MNPs) 310 have a high surface-to-volume ratio and a binding efficiency above 90%. The magnetic nanoparticles 310 are conjugated to the target analyte 322 via the immobilized antibodies or other binding pair members (e.g., via incubation in a suitable medium/buffer for a selected time and at a selected temperature depending on the particular analyte-binding pair member binding interaction), and thus the conjugated magnetic nanoparticles 330 become inherent magnetic biomarkers to the targets 322 (e.g., where the magnetic nanoparticle 310 component of the conjugate 330 serves as a detectable biomarker for the target 322), which biomarkers enhance the NMR signal of their conjugated targets 322. Magnetic particle-target complexes 330 are then detected by the portable NMR biosensor device 200. Suitably, as illustrated in FIG. 3, unbound MNPs 310 (which can affect the $T_2$ relaxation time of a sample population) can be separated (e.g., filtered) from analyte-MNP conjugates 330 (e.g., which are proportional the amount of analyte 322 in an original sample 320) prior to detection of the conjugates 330. In other embodiments, unbound MNPs 310 can remain in a sample containing analyte-MNP conjugates 330, with the resulting NMR relaxation signal still being able to differentiate samples 350 containing analyte-MNP conjugates 330 from those without conjugates 330, even in the presence of unbound MNPs 310. Regardless of whether the unbound MNPs 310 are to be present during NMR analysis, the original sample 320 is suitably washed/rinsed (e.g., with a suitable buffer, DI water, etc.), and the supernatant is discarded to provide the sample extract 350 for NMR analysis (e.g., once placed into a sample holder 80 of the NMR apparatus). Sample preparation takes 15 min and detection takes less than 1 min. The NMR system can be used to detect different biological and chemical targets such as bacteria, viruses, DNA, proteins, toxins, etc., based on suitable binding pair member-target analyte interaction appropriate to the target analyte of interest. The detection working principle is shown in FIG. 3.

Figure 4:
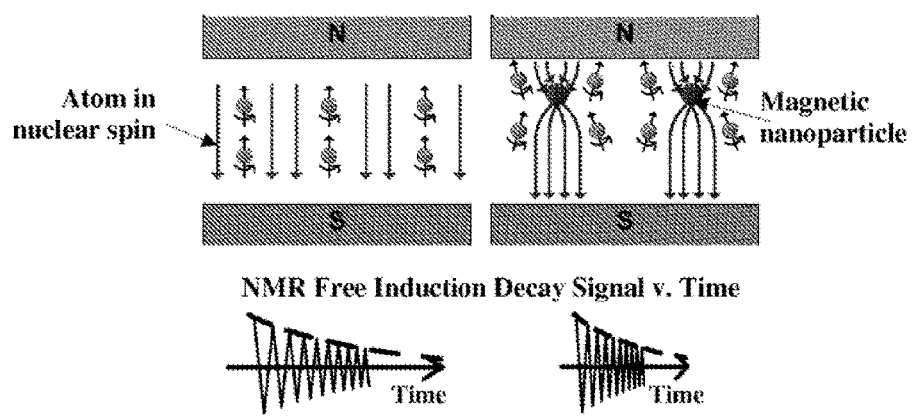
FIG. 4 is a schematic illustrating the influence of magnetic nanoparticles as target analyte labels on the NMR free induction decay time in a sample medium.

The conjugated magnetic nanoparticles (MNPs) become a magnetic biomarker for the presence of the target through NMR measurement. As shown in FIG. 4, the MNPs reduce the homogeneity of the static magnetic field strength and direction provided by the NMR permanent magnet according to their concentration (e.g., significantly dephasing the nuclear spins of water protons and decreasing the spin-spin relaxation time $T_2$). The NMR induction decay rate is very sensitive to field homogeneity disturbance, and this results in an observable increase in the decay rate, because the interaction and interference of inter-atom magnetic nuclear spin are significantly enhanced. A difference in decay rate which is caused by different target analyte concentrations can be efficiently detected by the high-power NMR device (e.g., the decay rate of the re-emitted NMR signal can be measured to determine pathogen concentration).

Figure 5:
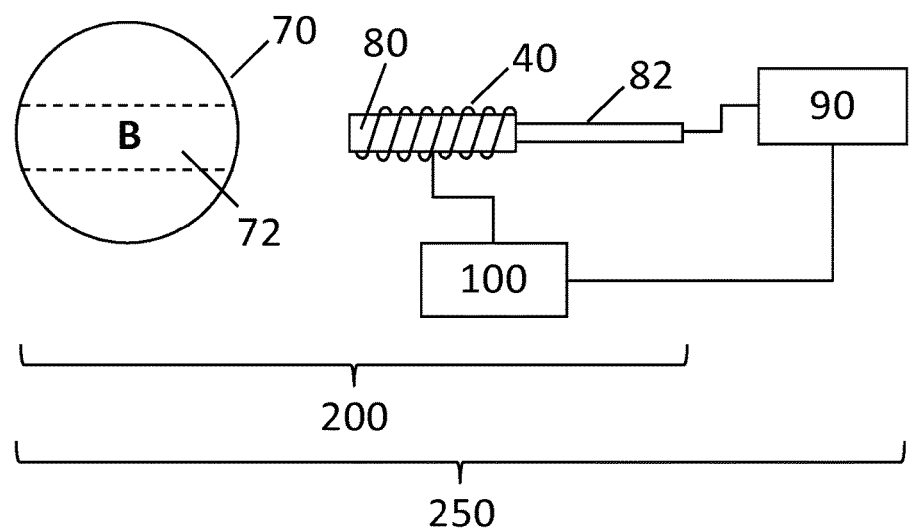
FIG. 5 is a schematic illustrating an NMR apparatus and system according to the disclosure.

An NMR apparatus 200 according to the disclosure is shown in FIG. 5. The system can be integrated in a portable size (e.g., 32 mm×24 mm×14 mm for the specific apparatus described in Example 1; can be reduced to a smaller size such as 20 mm×18 mm×8 mm or smaller if desired). Components illustrated in FIG. 5 include a permanent magnet 70 having a magnetic field B and an open cavity 72 for sample insertion, a tubular NMR sample holder 80 encircled by a solenoid as the NMR probe 40 (e.g., as a combined NMR transmission and receiving probe). The sample holder 80 can be mounted on a positioning means 82 such as an arm of an XYZ-positioner (e.g., including a motor for movement) for moving/positioning of the sample holder 80 out of the magnet cavity 72 for insertion of a sample to be analyzed (e.g., a sample extract 350 or otherwise for detection of a magnetic moiety therein) into the holder and for subsequent moving/positioning of the holder 80 into the cavity 72 for NMR analysis. The NMR probe 40 is coupled to/a component of the NMR transceiver 100, allowing NMR excitation and detection of the sample and any magnetic moieties therein (e.g., MNPs 310, analyte-MNP conjugates 330). In an embodiment, the NMR apparatus can be integrated into an NMR system 250 further including a computer 90 coupled to the NMR transceiver and optionally the positioning means 82 (e.g., to control the movement thereof). The computer can be a general purpose computer, for example including a processor and memory coupled to a computer readable storage medium encoded with one or more computer programs for controlling the NMR apparatus 200. For example the program can include instructions for execution by the processor to permit the computer 90 to control the NMR apparatus 200 and execute any, some, or all of the variously disclosed method steps for measuring an NMR signal in a sample (e.g., sample EM pulse excitation; NMR emission signal detection, data collection, data analysis, magnetic moiety detection/quantitation; frequency and power control loop set point selection, error function monitoring). The device is highly portable for the rapid detection of biological and chemical targets for healthcare, biodefense, biosafety, and environmental applications. The apparatus 200 or system 250 can be used to detect different biological and chemical materials 322 such as bacteria, viruses, DNA, proteins, toxins, and other contaminants. Antibodies or other binding pair members conjugated to the magnetic nanoparticles 310 provide the target specificity. Detection time is less than 1 minute once a sample is applied to the NMR sampling tube 80. The NMR tubes are inexpensive and are reusable with acetone rinsing. A suitable sample volume is 0.47 mL, although it can be reduced if desired.

Magnetic Nanoparticles

The NMR transceiver and apparatus as disclosed herein can be used in general to detect the presence of a magnetic moiety in a sample of interest. In a particular application illustrated herein, the NMR transceiver and apparatus can be used as a biosensor to detect the presence of a biological or chemical target analyte in a sample. To this end, the magnetic moiety detected by the NMR apparatus suitably includes a magnetic nanoparticle complexed/conjugated to the target analyte. Complexation/conjugation is suitably effected with a binding pair member (e.g., having specific or non-specific binding affinity to the analyte of interest, such as an analyte-specific antibody probe or oligonucleotide probe) bound or otherwise immobilized on the magnetic nanoparticle. In some embodiments, a polymer (e.g., conductive polymer) or other coating on the magnetic nanoparticle provides a convenient substrate for attachment or immobilization of the binding pair member to the magnetic nanoparticle). Examples of other non-polymeric magnetic nanoparticle coatings/shell materials that can be used to facilitate binding pair member attachment or immobilization include silica and various metals (e.g., gold, such as for attachment of a thiolated DNA/oligonucleotide probe or other analyte-specific binding pair member).

The magnetic nanoparticles according to the disclosure are not particularly limited and generally include any nano-sized particles (e.g., about 1 nm to about 1000 nm) that can be magnetized with an external magnetic/electrical field. The magnetic nanoparticles more particularly include superparamagnetic particles, which particles can be easily magnetized with an external magnetic field (e.g., to facilitate separation or concentration of the particles from the bulk of a sample medium) and then redispersed immediately once the magnet is removed (e.g., in a new (concentrated) sample medium). Thus, the magnetic nanoparticles are generally separable from solution with a conventional magnet. Suitable magnetic nanoparticles are provided as magnetic fluids or ferrofluids, and mainly include nano-sized iron oxide particles ($Fe_3O_4$ (magnetite) or $\gamma$-$Fe_2O_3$ (maghemite)) suspended in a carrier liquid. Such magnetic nanoparticles can be prepared by superparamagnetic iron oxide by precipitation of ferric and ferrous salts in the presence of sodium hydroxide and subsequent washing with water. A suitable source of $\gamma$-$Fe_2O_3$ is Sigma-Aldrich (St. Louis, Mo.), which is available as a nano-powder having particles sized at <50 nm with a specific surface area ranging from about 50 $m^2/g$ to about 250 $m^2/g$. Preferably, the magnetic nanoparticles have a small size distribution (e.g., ranging from about 5 nm to about 25 nm) and uniform surface properties (e.g., about 50 $m^2/g$ to about 245 $m^2/g$).

More generally, the magnetic nanoparticles can include ferromagnetic nanoparticles (i.e., iron-containing particles providing electrical conduction or resistance). Suitable ferromagnetic nanoparticles include iron-containing magnetic metal oxides, for example those including iron either as Fe(II), Fe(III), or a mixture of Fe(II)/Fe(III). Non-limiting examples of such oxides include FeO, $\gamma$-Fe$_2$O$_3$ (maghemite), and Fe$_3$O$_4$ (magnetite). The magnetic nanoparticles can also be a mixed metal oxide of the type M1$_x$M2$_{3-x}$O$_4$, wherein M1 represents a divalent metal ion and M2 represents a trivalent metal ion. For example, the magnetic nanoparticles may be magnetic ferrites of the formula M1Fe$_2$O$_4$, wherein M1 represents a divalent ion selected from Mn, Co, Ni, Cu, Zn, or Ba, pure or in admixture with each other or in admixture with ferrous ions. Other metal oxides include aluminum oxide, chromium oxide, copper oxide, manganese oxide, lead oxide, tin oxide, titanium oxide, zinc oxide and zirconium oxide, and suitable metals include Fe, Cr, Ni or magnetic alloys.

In embodiments where the magnetic nanoparticles include a conductive polymer coating/shell around a magnetic nanoparticle core, nanoparticulate composition can be generally formed by the polymerization of a conductive polymer monomer (e.g., aniline, pyrrole) in a solution (e.g., aqueous) containing the magnetic nanoparticles. The polymerization solution generally includes an acid dopant (e.g., HCl) to impart electrical conductivity to the resulting polymer. The polymerization reaction is preferably initiated by the addition of an oxidant (e.g., ammonium persulfate). Upon completion of the polymerization reaction, the solution contains the particulate composition in which the resulting conductive polymer is bound to the magnetic nanoparticles. The magnetic nanoparticles and the monomer can be combined in any suitable weight ratio in the polymerization solution so that the resulting particulate composition has a desired balance of magnetic, electrical, and particle size properties. For example, the weight ratio of monomer:magnetic nanoparticles in the polymerization solution (or conductive polymer:magnetic nanoparticles in the resulting particulate composition) preferably ranges from about 0.01 to about 10, more preferably from about 0.1 to about 1 or about 0.4 to about 0.8, for example about 0.6. Similarly, the magnetic nanoparticles (e.g., alone or with a polymer/conductive polymer coating) preferably range in size from about 1 nm to about 500 nm, more preferably about 10 nm to about 200 nm or about 50 nm to about 100 nm (e.g., representing bounds of a size distribution or a number- or weight-average size/diameter of the distribution).

Suitably, the magnetic nanoparticles further include a binding pair member bound or immobilized on an outer/external surface of the nanoparticles. The binding pair member is selected to be complementary to a target analyte so that the magnetic nanoparticles can be used for the selective detection of the target analyte in a sample.

An analyte (or target analyte) generally includes a chemical or biological material, including living cells, in a sample which is to be detected using the magnetic nanoparticles as a magnetic biomarker/label. The analyte can include pathogens of interest (e.g., *E. coli* O157:H7). The analyte also may be an antigen, an antibody, a ligand (i.e., an organic compound for which a receptor naturally exists or can be prepared, for example one that is mono- or polyepitopic, antigenic, or haptenic), a single compound or plurality of compounds that share at least one common epitopic site, and a receptor (i.e., a compound capable of binding to an epitopic or determinant site of a ligand, for example thyroxine binding globulin, antibodies, enzymes, Fab fragments, lectins, nucleic acids, protein A, complement component C1q). In some embodiments, the term "analyte" also can include an analog of the analyte (i.e., a modified form of the analyte which can compete with the analyte for a receptor) that can also be detected using the magnetic nanoparticles.

A sample generally includes an aliquot of any matter containing, or suspected of containing, the target analyte. For example, samples can include biological samples, such as samples from taken from animals (e.g., saliva, whole blood, serum, plasma, urine, tears, and the like), cell cultures, plants; environmental samples (e.g., water); and industrial samples. Samples may be required to be prepared prior to analysis according to the disclosed methods. For example, samples may require extraction, dilution, filtration, centrifugation, and/or stabilization prior to analysis. For the purposes herein, "sample" can refer to either a raw sample as originally collected or a sample resulting from one or more preparation techniques applied to the raw sample.

The binding pair member (or specific binding partner) generally includes one of two different molecules, each having a region or area on its surface or in a cavity that specifically binds to (i.e., is complementary with) a particular spatial and polar organization of the other molecule. The binding pair members can be referenced as a ligand/receptor (or antiligand) pair. These binding pair members include members of an immunological pair such as antigen-antibody. Other specific binding pairs such as biotin-avidin (or derivatives thereof such as streptavidin or neutravidin), hormones-hormone receptors, IgG-protein A, polynucleotide pairs (e.g., DNA-DNA, DNA-RNA), DNA aptamers, and whole cells are not immunological pairs, but can be used as binding pair members within the context of the present disclosure.

Preferably, the binding pair members are specific to each other and are selected such that one binding pair member is the target analyte of interest and the other binding pair member is the constituent bound to the conductive polymer of the particulate composition. Binding specificity (or specific binding) refers to the substantial recognition of a first molecule for a second molecule (i.e., the first and second members of the binding pair), for example a polypeptide and a polyclonal or monoclonal antibody, an antibody fragment (e.g., a Fv, single chain Fv, Fab', or F(ab')$_2$ fragment) specific for the polypeptide, enzyme-substrate interactions, and polynucleotide hybridization interactions. Preferably, the binding pair members exhibit a substantial degree of binding specificity and do not exhibit a substantial amount of non-specific binding (i.e., non-covalent binding between molecules that is relatively independent of the specific structures of the molecules, for example resulting from factors including electrostatic and hydrophobic interactions between molecules).

Substantial binding specificity refers to an amount of specific binding or recognition between molecules in an assay mixture under particular assay conditions. Substantial binding specificity relates to the extent that the first and second members of the binding pair to bind only with each other and do not bind to other interfering molecules that may be present in the analytical sample. The specificity of the first and second binding pair members for each other as compared to potential interfering molecules should be sufficient to allow a meaningful assay to be conducted for the target analyte. The substantial binding specificity can be a function of a particular set of assay conditions, which includes the relative concentrations of the molecules, the time and temperature of an incubation, etc. For example, the reactivity of one binding pair member with an interfering molecule as compared to that with the second binding pair member is preferably less than about 25%, more preferably less than about 10% or about 5%.

A preferred binding pair member is an antibody (an immunoglobulin) that specifically binds to and is thereby defined as complementary with a particular spatial and polar organization of another molecule (e.g., an antigen). Antibodies generally include Y-shaped proteins on the surface of B cells that specifically bind to antigens such as bacteria, viruses, etc. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b, IgG3, IgM, etc. Fragments thereof may include Fab, Fv and F(ab')$_2$, and Fab'. In addition, aggregates, polymers, and conjugates of immunoglobulins or their fragments can be used where appropriate so long as binding affinity for a particular molecule is maintained.

The binding pair member that is specific to the target analyte can be bound to the magnetic nanoparticles (e.g., directly or indirectly via a polymer/conductive polymer coating on the nanoparticles) by any of a variety of methods known in the art appropriate for the particular binding pair member (e.g., antibody, DNA oligonucleotide). For example, antibodies can be bound to a conductive polymer coating on the magnetic nanoparticles by incubating the antibodies in a buffer (e.g., a phosphate buffer at a pH of about 7.4 containing dimethylformamide and lithium chloride) suspension of the particulate composition. Similarly, oligonucleotides can be incubated in a buffer (e.g., an acetate buffer at a pH of about 5.2) suspension of the particulate composition that also includes an immunoconjugating agent (e.g., 1-ethyl-3-(3-dimethylaminopropyl) carbodiimide hydrochloride ("EDAC")). After a suitable incubation period (i.e., depending on the rate of binding between the binding pair member and the conductive polymer) the resulting BEAM nanoparticles can be blocked, washed, centrifuged, and then stored as a suspension (e.g., in aqueous LiCl for an antibody on a phosphate-buffered saline ("PBS") solution for an oligonucleotide).

EXAMPLES

The following examples illustrate the disclosed processes, apparatus, systems, and compositions, but are not intended to limit the scope of any claims thereto.

Example 1

NMR Apparatus and Detection of *E. coli* O157:H7

This example illustrates the use of an NMR apparatus according to the disclosure as a versatile and powerful analytical technology to non-destructively study biological materials in turbid sample matrices. A portable NMR-based biosensor is disclosed using antibody-functionalized magnetic nanoparticles as biomarkers. The NMR biosensor operates at 0.47 Tesla of magnetic strength with an embedded control of excitation power and frequency to compensate for environmental fluctuations, such as ambient magnetic field and temperature fluctuations. In the example, the NMR apparatus was used to detect *E. coli* O157:H7 bacteria in broth and milk. A rapid separation method was developed using a nanoporous syringe filter and magnetic separation to remove excess magnetic nanoparticles. The NMR biosensor was capable of detecting *E. coli* O157:H7 at low concentrations in 100 milliseconds. With portable size and embedded control, the NMR biosensor can be used for rapid on-field detection of disease-causing pathogens and other contaminants for healthcare, defense, and safety applications.

Nuclear Magnetic Resonance (NMR) is a powerful technique to analyze the magnetic properties of atomic nuclei and determine physical and chemical properties of atoms or molecules. As its signal is capable of penetrating a turbid raw sample, NMR instruments have wide applications in biomedical diagnosis, which can simplify sample preparation process, save analysis time. However, the commercial NMR systems are expensive, bulky and heavy (around 1,000 kg), which limit their application for portable diagnosis.

This example discloses a portable NMR including an NMR transceiver and an NMR probe for a biosensor to detect *Escherichia coli* O157:H7 bacteria using magnetic nanoparticles as a biomarker. *E. coli* O157:H7 is one of the major bacterial pathogens, which has caused foodborne outbreaks in the USA, UK and other countries. In 2009, food contamination *E. coli* outbreaks in beef occurred in 8 states of the USA for a total of 26 identified cases and 2 deaths, and caused the Centers for Disease Control and Prevention (CDC) to issue a health alert, and a recall of approximately 545,699 pounds of ground beef products. In 1996, an *E. coli* outbreak in Scotland caused 7 deaths and left hundreds more infected, due to poor hygienic meat preparation processes. In recent years, *E. coli* O157:H7 annually causes food outbreaks in the US for different food products, including fresh spinach (2006), pizza and ground beef (2007), beef (2008), cookie dough and beef (2009), cheese and beef (2010), and sausage and hazelnut (2011). The annual cost of *E. coli* O157:H7 outbreaks including premature deaths, medical care, and product recall was estimated to be $405 million.

The detection of *E. coli* O157:H7 is time-consuming, and it requires complex instruments and extensive training. The Sorbitol-MacConkey (SMAC) agar method is used for identification, but it takes about 2-4 days, including culture, morphological identification, and confirmation techniques. The polymerase chain reaction (PCR) based detection assays are sensitive and accurate. However, the PCR techniques require complex sample preparation steps, such as DNA extraction and amplification, which increase additional diagnosis time. Fast detection methods have been reported based on immunological detection. However, most of these diagnosis systems have a sensitivity limit greater than 100 CFU/mL, a detection time of 1 hour, and are not applicable for on-field applications. In order to minimize the spread of infection and costly product recall, a rapid, sensitive, and portable detection of *E. coli* O157:H7 is essential in food supply and healthcare applications.

Design of Portable NMR Biosensor: A nuclear magnetic resonance system was designed consisting of a proton NMR probe, a high-power and high-sensitivity transceiver, and a FPGA-based pulse controller and communication interface (e.g., FPGA incorporating glue logic managing communication and data acquisition of the biosensor). The system utilized an NdFeB permanent magnet (PM-1055, Metrolab Instruments Inc.), with a magnetic field strength of 0.49 Tesla, a size of Ø80×H55 mm, and weighed 1,250 g. Based on the magnet's homogeneous region size as measured by a gauss meter, a proton NMR probe was designed and consisted of a solenoid coil with size of Ø5×L5 mm, and matching networks using high Q capacitor trimmers, to achieve optimal signal-to-noise ratio (SNR). The input impedance was tuned to be 50 ohms for optimal power output efficiency and the overall quality factor was optimized to be 686.8 measured using an Agilent E5062A Network Analyzer.

In the transmitter design, the NMR excitation signal was generated using the Direct Digital Synthesizer (DDS) for variable output frequency up to 50 MHz (1 µHz tuning accuracy) with excellent frequency stability. A linear power amplifier (LPA) was implemented for configurable output power up to 50 Watts to amplify sinusoidal or arbitrary waveforms (e.g., sine waveform for potential application of magnetic resonance imaging). A transmit/receive (T/R) switch (RF switch; 33.40 dB attenuation) was designed using a high speed crossed diode and quarter wavelength transmission line to protect the low noise amplifier during high power excitation and to block the noise from the LPA during receiving.

In the receiver design, the NMR signal around 0.1 µV was amplified by a low-noise amplifier (LNA) and a high Q (quality; low bandwidth) bandpass filter (BPF), and detected by quadrature amplitude demodulation (QAM) to obtain phase information and enhance sensitivity. With excellent concurrent calculation capability and high integration, an embedded system was designed in a FPGA using a multilayer state machine to receive commands and display via HyperTerminal, control the DDS frequency and amplifier gain, and provide precise deblanking pulse control and versatile NMR pulse sequence control.

The precision output frequency control provided self-adaptability to frequency shift caused by temperature induced magnetic field changes, which is essential for portable applications. The high speed pulse width control allowed versatile NMR applications (e.g., T1, T2 determination). The high power capability enabled the system to measure an NMR signal in less detectable molecules (e.g., glycerin), and in a higher sample volume for a better signal-to-noise ratio. With appropriable NMR probes, the system has potential application to detect other magnetic atoms and perform magnetic resonance imaging.

The portable NMR system is illustrated in FIG. 5. The magnet holder, NMR probe holder, and gauss meter probe holder for XYZ linear positioner were designed using aluminum and wood to determine the most homogeneous region of the magnet in order to optimize NMR signal. The apparatus was built using low cost amplifiers including a 50B power amplifier (1.8 MHz to 45 MHz, RF pulse; Henry Radio), and an AU-1467 linear amplifier (65 dB, NF 1.2 dB; Miteq Inc.). The overall size of the apparatus was 32 mm×24 mm×14 mm. The system could be integrated in a mini personal computer enclosure to an estimated size of 20 mm×18 mm×8 mm for better portability and electromagnetic compatibility (EMC) performance. The total pathogen detection time of the system was 34 minutes (30 min for incubation, 3 min for separation and 1 min for NMR detection). Low cost, commercially available 5-mm NMR tubing was used as a test sample holder and was shown to be reusable after acetone washing. The sample volume of the prototype system was 100 µL. It could be further reduced by using thinner NMR tubes if necessary (e.g., a 20 µL NMR tube).

Functionalization of Magnetic Nanoparticles with Antibody: To functionalize the magnetic nanoparticles with antibody, 2.5 mg of paramagnetic iron oxide ($Fe_2O_3$; 20 nm average size) and polyaniline (PANi) conjugate were added into a 1.5 mL test tube. The PANi-coated MNPs were formed according to a process as generally disclosed in Alocilja et al. U.S. Publication Nos. 2008/0314766 and 2009/0123939 and then filtered to a size of about 80 nm. The MNPs ($Fe_2O_3$) and PANI-coated MNPs had saturation magnetization values of 64.4 emu/g and 44.1 emu/g, respectively. Then 150 µL of 0.1 M phosphate buffer solution (PBS) was added to the test tube and sonicated for 15 minutes to evenly disperse the particles. Then 100 µL of 2.5 mg/mL monoclonal anti E. coli O157:H7 antibody in PBS was added to the test tube and then incubated in a hybridization oven at 25° C. at 30 rpm for 1 hour. This prepared solution was stored at 4° C. in a refrigerator until needed.

Test Pathogens: E. coli O157:H7 was obtained from the collection of the Nano-Biosensors Laboratory at Michigan State University. E. coli O157:H7 test strains were inoculated using sterile loop into 10 mL of Tryptic soy nutrient broth from Difco Laboratories (Detroit, Mich.) and incubated for 24 h at 37° C. to make a stock culture. The stock culture was then serially diluted in 0.1% peptone water in a logarithmic scale to obtain different concentrations. All of the experiments were performed in a certified Biological Safety Level II laboratory.

Magnetic Pathogen Separation: For pathogen labeling, the antibody-functionalized MNPs were added into a sample solution and incubated at 25° C. at 60 rpm for 30 minutes to allow conjugation between the MNPs and pathogens. Then the incubated solution was filtered using a syringe filter with optimal pore size of 0.45 µm for both pathogen capture and nanoparticle separation. After a wash step using PBS to separate impurities and unbound magnetic nanoparticles, the syringe filter was backflushed using PBS to release the MNP-pathogen conjugates for further testing using NMR. During the process, a strong-field magnet was used to manipulate the MNPs in solution in order to facilitate the separation of unbound MNPs, hold the MNP-pathogen conjugates during washing, and help elute the MNP-labeled pathogen. The filter based magnetic separation process is illustrated in FIG. 4.

Sensor Architecture and Detection Principle: After the filter-based magnetic separation process, the interference of unbound MNPs was effectively reduced, and MNPs in the eluted solution were proportional to the pathogen concentration. As paramagnetic material, the MNPs induced spatial and temporal disturbance in the homogeneity and strength of the local magnetic field (FIG. 4). Due to the high surface area-to-volume ratio, this disturbance introduced precession frequency variations in millions of protons of the surrounding water molecules, which accelerated the decay of the spin system's phase coherence. The MNP's concentration has a linear relationship to the water proton's spin-spin relaxation time, T2. Therefore, the concentration of target pathogen in test solution could be measured from T2 signal using the portable NMR biosensor.

Detection and Data Analysis: The NMR biosensor signal was measured using a digital oscilloscope (Model Agilent DSO1024A, Agilent Technologies, Santa Clara, Calif.) connected to the NMR's signal output using a BNC cable. For the biosensor test, a volume of 100 µL of the test solution by immunomagnetic separation was applied to the biosensor. The NMR spin-echo relaxation signal was recorded by the oscilloscope, which is controlled by the FPGA synchronization signal. The whole process of NMR relaxation was less than 1 minute. For data analysis, a minimum of three replications were performed for each experiment. All biosensors were calibrated using a control sample which consisted of immunomagnetic-separated solution prepared using the same test solution but without the pathogen. Standard deviations and mean values for the data of each experiment were calculated. Statistical analysis was performed based on a single factor analysis of variance using ANOVA.

Results and Discussion: The NMR relaxation signals for a pathogen sample (MNP-pathogen conjugates; panel A) and a control sample (unconjugated MNPs; panel B) are show in FIG. 6. The *E. coli* O157:H7 sample with a concentration of 226 CFU/mL had a T2 relaxation time of 55.6 ms (FIG. 6(A)). The control sample which contained the same amount of magnetic nanoparticles but without bacteria had a T2 relaxation time of 102.7 ms (FIG. 6(B)). The T1 time of the control sample was 54.1% of that of the pathogen sample.

Figure 6:
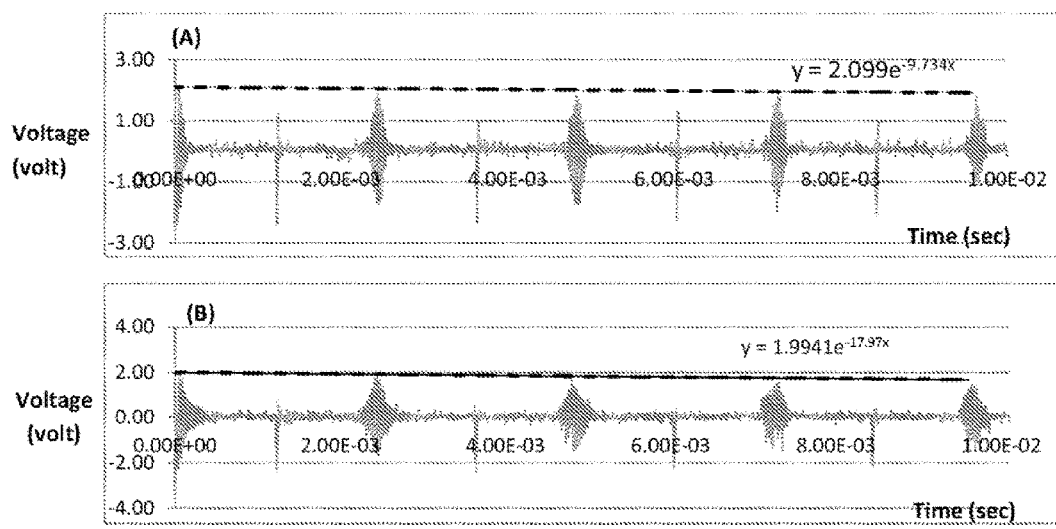
FIG. 6 includes graphs illustrating the NMR relaxation signal of samples including MNP-pathogen conjugates (A) and control MNPs without pathogen (B).

The spin-spin relaxation has exponential decay, which can be modeled by the following Equation 1: $M(t)=M_0 e^{(-t/T2)}$. M(t) is the nuclear spin magnetization vector as a function of time t, $M_0$ is the initial nuclear spin magnetization vector, and T2 is the spin-spin relaxation time constant. The relaxation time T2 is not related to M or $M_0$; it is determined by the signal envelope of the NMR decay, which can be obtained by curve fitting of the NMR signal (e.g., as illustrated in FIG. 6). Therefore, T2 can be calculated as the reciprocal of the time constant obtained by the exponential curve fitting for the envelope of the spin echo signal as shown in FIGS. 6 (A) and (B).

Tables 1 and 2 below show the NMR relaxation time measured using the magnetic nanoparticle-based NMR biosensor for whole milk and water samples of different concentrations *E. coli* O157:H7 bacteria. The average relaxation time T2 of three replicates was plotted for the control and the food samples, inoculated with bacteria concentration ranging from $7.6 \times 10^1$ CFU/mL to $7.6 \times 10^7$ CFU/mL for water samples and from $10.8 \times 10^1$ CFU/mL to $10.8 \times 10^7$ CFU/mL for whole milk samples. As shown in the tables, the relaxation values measured for bacteria samples are much lower than the values for control sample which has no bacteria. The reduced relaxation times support the formation of magnetic nanoparticles bonded to target bacteria, which changes its nearby magnetic field and affects the nucleus spin of hydrogen atoms in surrounding water molecules.

TABLE 1

NMR Biosensor Relaxation Times of
MNP/*E. coli* Conjugates in Water

| Bacteria Concentration (CFU/ml) | Relaxation Time, T2 (ms) |
| --- | --- |
| 0 (control; MNPs only) | 98.91 |
| $7.6 \times 10^1$ | 88.33 |
| $7.6 \times 10^2$ | 53.83 |
| $7.6 \times 10^3$ | 42.27 |
| $7.6 \times 10^4$ | 51.04 |
| $7.6 \times 10^5$ | 56.88 |
| $7.6 \times 10^6$ | 34.96 |
| $7.6 \times 10^7$ | 28.55 |

TABLE 2

NMR Biosensor Relaxation Times of
MNP/*E. coli* Conjugates in Milk

| Bacteria Concentration (CFU/ml) | Relaxation Time, T2 (ms) |
| --- | --- |
| 0 (control; MNPs only) | 89.67 |
| $10.8 \times 10^1$ | 81.80 |
| $10.8 \times 10^2$ | 59.97 |
| $10.8 \times 10^3$ | 40.47 |
| $10.8 \times 10^4$ | 28.27 |
| $10.8 \times 10^5$ | 37.18 |
| $10.8 \times 10^6$ | 26.53 |
| $10.8 \times 10^7$ | 25.79 |

Summary: This example illustrates an integrated design of an NMR biosensor combining antibody-functionalized magnetic nanoparticles and filter-based magnetic separation. The detection of the biosensor system is fast, which includes a magnetic concentration time of 33 min followed by a signal detection of 1 min. Due to the unique signal penetration capability of NMR, the sensitivities for water and food (milk) samples are not significantly different (i.e.,. 76 CFU/mL and 108 CFU/mL, respectively), and the detection method can be extended to more complex matrices. The detection application can be extended to other microbial or viral organisms by appropriate adaption of the corresponding antibodies immobilized on the capture/biomarker MNPs.

Example 2

Detection of IP-10 Biomarker

Interferon gamma-induced protein 10 (IP-10) is used as an illustrative biomarker sample analyte in this example. IP-10 is a protein that is commonly present in bodily fluids (e.g., blood or urine of a mammal such as a human) at relatively low levels in healthy patients, but the IP-10 level in a patient increases as a response to infection. Thus, an assay to detect levels of IP-10 in a particular patient or population of patients can be used to detect, predict, or confirm the presence of an infection in the patient/population either before or after the onset of outwardly detectable symptoms of the same (e.g., when the IP-10 sample concentration exceeds a threshold level associated with infection).

The NMR apparatus of Example 1 was used to detect IP-10 in water samples at concentrations ranging from 0.01 ng/ml to 100 ng/ml. PANi-coated MNPs as described in Example also were used to extract the IP-10 analyte from a given sample, with the exception that the MNPs were functionalized with anti-IP-10 antibodies instead of anti-*E. coli* antibodies. In this example and Example 1, the conductive polymer (PANi) coating on the MNPs provides a convenient substrate for antibody immobilization/attachment, but the electrically active/conductive nature of the polymer coating need not form a basis for analyte detection (e.g., the PANi need not serve as a signal transducer for analyte detection and other methods for immobilizing antibodies (or other binding partners specific to a particular analyte) to the MNP substrate can be used as desired).

The method of detection for the IP-10 analyte was similar to that of Example 1. Namely, antibody-functional MNPs were added to water samples containing known concentrations of IP-10 and incubated to under conditions to form MNP-analyte conjugates. As illustrated in FIG. 3 and described in Example 1, a magnet was used to facilitate the washing of MNPs to discard the sample supernatant and provide a concentrated MNP suspension. In contrast to Example 1, however, unbound MNPs were not separated (e.g., by filtration) from MNP-analyte conjugates. Thus, the concentrated MNP suspension tested in the NMR apparatus contained a combination of both unbound MNPs and MNP-analyte conjugates (i.e., depending on the initial concentration of MNPs added to the sample and the concentration of IP-10 analyte in the sample and forming the resulting conjugate). The NMR analysis and measurement of the T2 relaxation time for the concentrated MNP suspension is summarized in Table 3 below. As shown in the table, the NMR analysis is sensitive enough to differentiate between unbound MNPs and MNP-analyte conjugates. Specifically, the control sample (i.e., containing only unbound MNPs) exhibits a distinct T2 relaxation time relative to relaxation times measured for samples containing a combination unbound MNPs and MNP-analyte conjugates (i.e., where the total amount of MNPs between those that are unbound and those that are conjugated is the same for all runs in Table 3). As shown in Table 3, IP-10 concentrations as low as 0.01 ng/ml were differentiable from the control. This illustrates that the NMR assay can be further streamlined in that it can omit the usual separation step between unbound MNPs (or other labels/biomarker) and MNP-analyte conjugates while still enabling the positive identification and quantitation of analyte-bound conjugates (i.e., in the presence of other unbound biomarkers).

TABLE 3

NMR Biosensor Relaxation Times of MNP/IP-10 Conjugates in Water

| IP-10 Concentration (ng/ml) | Relaxation Time, T2 (ms) |
|---|---|
| 0 (control; MNPs only) | 61.4 |
| 0.01 | 50.8 |
| 0.1 | 44.6 |
| 1 | 34.7 |
| 10 | 33.4 |
| 100 | 33.3 |

At IP-10 concentrations above about 1 nm/ml, the T2 relaxation time did not substantially continue to decrease, suggesting that the IP-10 amount originally present in the sample was in sufficient excess to saturate the binding capacity of the unbound MNPs initially added to the sample (i.e., substantially all of the MNPs in the test sample are conjugated with IP-10 and there are substantially no remaining unbound MNPs). Of course, the initial amount of unbound MNPs could be adjusted accordingly depending on concentration range where it is desired to generate a concentration-dependent response for the relaxation time (e.g., increased initial unbound MNPs to differentiate IP-10 concentrations in the range of 1 ng/ml to 100 ng/ml). Notably, the results in Table 3 illustrate that the NMR biosensor analysis of IP-10 provides both a lower detection limit (about 0.01 ng/ml) and greater dynamic range (about 0.01 ng/ml to about 1 ng/ml or about two orders of magnitude) relative to a comparable ELISA assay for IP-10 (e.g., generally having a detection limit of about 0.1 ng/ml and a dynamic range of about 0.1 ng/ml to about 1 ng/ml or about one order of magnitude).

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, systems, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

What is claimed is:

1. A method for measuring nuclear magnetic resonance (NMR) in a sample, the method comprising:
  (a) providing an NMR apparatus comprising:
    (i) a nuclear magnetic resonance (NMR) transceiver comprising:
      (A) a variable-frequency electromagnetic (EM) signal generator comprising a frequency input and an EM signal output;
      (B) a frequency controller comprising a frequency output coupled to the frequency input of the variable-frequency EM signal generator, a frequency set-point input, and a frequency measurement input;
      (C) an NMR transmission probe comprising an EM signal input coupled to the EM signal output of the variable-frequency EM signal generator;
      (D) an NMR receiving probe comprising an EM signal output; and
      (E) a mixer comprising a first input coupled to the EM signal output of the NMR receiving probe, a second input coupled to the EM signal output of the variable-frequency EM signal generator, and a mixed EM signal output coupled to the frequency measurement input of the frequency controller;
    (ii) a magnet having a magnetic field; and
    (iii) a sample container positionable in the magnetic field and proximate to the NMR transmission probe and the NMR receiving probe;
  (b) selecting the frequency set-point input to the frequency controller;
  (c) placing a sample to be measured for the presence of a magnetic moiety in the sample container;
  (d) exciting the sample with an EM signal delivered from the NMR transmission probe, the EM signal having a selected frequency and a selected power;
  (e) detecting an NMR signal emitted from the excited sample with the NMR receiving probe; and
  (f) determining a new selected frequency for the EM signal delivered from the NMR transmission probe with the frequency controller and an error function determined from (i) the frequency set-point input and (ii) a mixed EM signal from the delivered EM signal and the emitted NMR signal as the frequency measurement input.

2. The method of claim 1, further comprising:
(g) determining whether the magnetic moiety is present in the sample.

3. The method of claim 1, wherein:
(i) the NMR transceiver further comprises:
(F) a power amplifier comprising an EM signal input coupled to the signal output of the variable-frequency EM signal generator, an amplifier gain input, and an amplified EM signal output;
(G) a directional coupler comprising an EM signal input coupled to the amplified EM signal output of the power amplifier, an EM signal output coupled to the EM signal input of the NMR transmission probe, and a voltage output; and
(H) a gain controller comprising a gain output coupled to the amplifier gain input of the power amplifier, a voltage set-point input, and a voltage measurement input coupled to the voltage output of the directional coupler; and
(ii) the method further comprises determining a new selected power for the EM signal delivered from the NMR transmission probe with the gain controller and an error function determined from (A) the voltage set-point input and (B) the voltage output from the directional coupler as the voltage measurement input.

4. The method of claim 1, wherein:
(i) the NMR transmission probe and the NMR receiving probe are in the form of a combined NMR probe coupled to a switch switchable between at least a transmit state and a receive state;
(ii) in the transmit state, the NMR probe is coupled to the EM signal output of the variable-frequency EM signal generator;
(iii) in the receive state, the NMR probe is coupled to the first input of the mixer; and
(iv) the sample container is mountable to the combined NMR probe.

5. The method of claim 1, wherein the magnetic moiety comprises a magnetic nanoparticle-analyte complex comprising a magnetic nanoparticle bound to a target analyte.

6. The method of claim 5, wherein the sample is substantially free from magnetic nanoparticles not bound to the target analyte.

7. The method of claim 5, wherein the sample further comprises magnetic nanoparticles not bound to the target analyte.

8. The method of claim 7, further comprising:
repeating the method for measuring for nuclear magnetic resonance in a separately analyzed control sample, the control sample comprising magnetic nanoparticles (i) only in the form of magnetic nanoparticles not bound to the target analyte and (ii) in the same amount as total magnetic nanoparticles present in the sample; and
comparing the NMR measurement for the sample with the NMR measurement for the control sample to determine whether the magnetic nanoparticle-analyte complex is present in the sample.

9. The method of claim 5, wherein the target analyte is selected from the group consisting of bacteria, viruses, oligonucleotides, polynucleotides, proteins, enzymes, and combinations thereof.

10. The method of claim 5, wherein the magnetic nanoparticle comprises: (i) a magnetic nanoparticle core, (ii) a conductive polymer shell bound to the magnetic nanoparticle core, and (iii) a binding pair member bound to the conductive polymer shell.

11. The method of claim 5, wherein the magnetic nanoparticle comprises: (i) a magnetic nanoparticle core, and (ii) a binding pair member complementary to the target analyte and immobilized on the magnetic nanoparticle core.

12. The method of claim 1, comprising selecting the frequency set-point input corresponding to the ambient temperature during measurement.

13. The method of claim 1, comprising selecting the frequency set-point input to have a value ranging from 0.01 kHz to 10 kHz.

14. The method of claim 1, wherein the sample comprises a liquid sample medium.

15. The method of claim 1, comprising performing the method without active or passive temperature control.

16. A nuclear magnetic resonance (NMR) transceiver comprising:
(a) a variable-frequency electromagnetic (EM) signal generator comprising (i) a frequency input and (ii) an EM signal output;
(b) a frequency controller comprising (i) a frequency output coupled to the frequency input of the variable-frequency EM signal generator, (ii) a frequency set-point input, and (iii) a frequency measurement input;
(c) an NMR transmission probe comprising an EM signal input coupled to the EM signal output of the variable-frequency EM signal generator;
(d) an NMR receiving probe comprising an EM signal output; and
(e) a mixer comprising (i) a first input coupled to the EM signal output of the NMR receiving probe, (ii) a second input coupled to the EM signal output of the variable-frequency EM signal generator, and (iii) a mixed EM signal output coupled to the frequency measurement input of the frequency controller.

17. The NMR transceiver of claim 16, wherein:
(i) the NMR transmission probe and the NMR receiving probe are in the form of a combined NMR probe coupled to a switch switchable between at least a transmit state and a receive state;
(ii) in the transmit state, the NMR probe is coupled to the EM signal output of the variable-frequency EM signal generator; and
(iii) in the receive state, the NMR probe is coupled to the first input of the mixer.

18. The NMR transceiver of claim 17, wherein the NMR probe comprises a solenoid coil.

19. The NMR transceiver of claim 16, further comprising:
(f) a power amplifier comprising (i) an EM signal input coupled to the signal output of the variable-frequency EM signal generator and (ii) an amplified EM signal output coupled to the EM signal input of the NMR transmission probe.

20. The NMR transceiver of claim 16, further comprising:
(f) a power amplifier comprising (i) an EM signal input coupled to the signal output of the variable-frequency EM signal generator, (ii) an amplifier gain input, and (iii) an amplified EM signal output;
(g) a directional coupler comprising (i) an EM signal input coupled to the amplified EM signal output of the power amplifier, (ii) an EM signal output coupled to the EM signal input of the NMR transmission probe, and (iii) a voltage output; and
(h) a gain controller comprising (i) a gain output coupled to the amplifier gain input of the power amplifier, (ii) a voltage set-point input, and (iii) a voltage measurement input coupled to the voltage output of the directional coupler.

21. The NMR transceiver of claim 16, wherein the variable-frequency EM signal generator is capable of delivering an EM signal to the NMR transmission probe input with a power ranging from 1 W to 100 W.

22. The NMR transceiver of claim 16, wherein the variable-frequency EM signal generator is capable of generating an EM signal with a frequency ranging from 5 MHz to 200 MHz.

23. A nuclear magnetic resonance (NMR) apparatus comprising:
(a) the nuclear magnetic resonance (NMR) transceiver according claim 16;
(b) a magnet having a magnetic field; and
(c) a sample container positionable in the magnetic field and proximate to the NMR transmission probe and the NMR receiving probe.

24. The NMR apparatus of claim 23, wherein:
(i) the NMR transmission probe and the NMR receiving probe are in the form of a combined NMR probe coupled to a switch switchable between at least a transmit state and a receive state;
(ii) in the transmit state, the NMR probe is coupled to the EM signal output of the variable-frequency EM signal generator;
(iii) in the receive state, the NMR probe is coupled to the first input of the mixer; and
(iv) the sample container is mountable to the combined NMR probe.

25. The NMR apparatus of claim 23, wherein the magnet comprises a permanent magnet.

26. The NMR apparatus of claim 23, wherein the magnetic field ranges in strength from 0.01 T to 1 T.

27. A nuclear magnetic resonance (NMR) measurement system comprising:
(a) the NMR apparatus according to claim 23; and
(b) a computer comprising a processor and memory coupled to a computer readable storage medium encoded with a computer program, the program comprising instructions that, when executed by the processor, cause the computer to control the NMR apparatus and execute one or more method steps for measuring nuclear magnetic resonance (NMR) in a sample.

* * * * *